United States Patent [19]

Menn

[11] 3,968,209
[45] July 6, 1976

[54] ANTHELMINTIC USE OF PHOSPHORYLATED THIOUREAS

[75] Inventor: Julius J. Menn, Saratoga, Calif.

[73] Assignee: Stauffer Chemical Company, Westport, Conn.

[22] Filed: Oct. 3, 1975

[21] Appl. No.: 619,261

[52] U.S. Cl. ............................................... 424/211
[51] Int. Cl.² ........................................ A61K 31/66
[58] Field of Search ..................................... 424/211

[56] References Cited
UNITED STATES PATENTS

| | | | |
|---|---|---|---|
| 3,711,578 | 1/1973 | Pianka | 424/211 |
| 3,758,644 | 9/1973 | Stolzer et al. | 424/211 |

*Primary Examiner*—Sam Rosen
*Attorney, Agent, or Firm*—Joel G. Ackerman

[57] ABSTRACT

A method of controlling helminth infections in animals comprising orally administering to said animal an anthelmintically effective amount of a compound having the formula

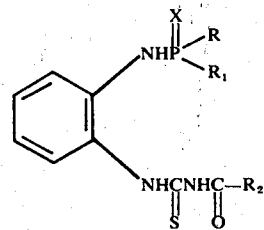

in which X is sulfur or oxygen, R and $R_1$ are independently lower alkyl or lower alkoxy, and $R_2$ is lower alkoxy.

3 Claims, No Drawings

ANTHELMINTIC USE OF PHOSPHORYLATED THIOUREAS

BACKGROUND AND PRIOR ART

This invention relates to the treatment of helminth infections (helminthiasis) in animals. The term helminth refers to nematodes, roundworms, flatworms and other worms which infest the gastro-intestinal tract, lung, liver and other organs. Animals attacked by such helminths may show retarded growth or poor increase in weight because of insufficient utilization of feed given to them; moreover injuries may occur which can result in the death of the animals. Compounds such as hygromycin, phenothiazine, piperazine, and pyridyl benzimidazoles, and their derivatives have been described as useful in the treatment of this disease.

It has now been found that a group of phosphorylated thioureas which have hitherto been found useful as fungicides and biocides also possess anthelmintic activity in animals, particularly in poly-gastric animals such as sheep, cattle, goats and the like. Compounds of this type and methods for preparing them are contained in U.S. Pat. No. 3,767,734 of Alexander Mihailovski and Don R. Baker.

SUMMARY OF THE INVENTION

This invention comprises a method of controlling helminth infections in animals comprising orally administering to said animal an anthelmintically effective amount of a compound having the formula

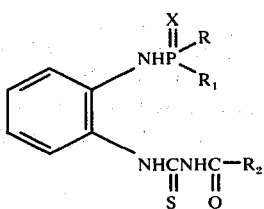

in which X is oxygen or sulfur, R and $R_1$ are independently lower alkyl or lower alkoxy, and $R_2$ is lower alkoxy. R and $R_1$ may be the same or different moieties. By the terms "lower alkyl" and "lower alkoxy" are meant such moieties having from 1 to about 4 carbon atoms, such as methyl, ethyl, n-propyl, isopropyl, n-butyl, and methoxy, ethoxy, n-propoxy, isopropoxy, n-butoxy, isobutoxy, and the like.

DETAILED DESCRIPTION OF THE INVENTION

Compounds having the above formula which have been found effective in the treatment of helminths in animals are listed in the following Table 1.

Table 1

| Compound No. | X | R | $R_1$ | $R_2$ | m.p., °C |
|---|---|---|---|---|---|
| 1 | O | $OC_2H_5$ | $OC_2H_5$ | $OCH_3$ | 154–155* |
| 2 | O | $OC_2H_5$ | $OC_2H_5$ | $OC_2H_5$ | 163–166* |
| 3 | S | $OC_2H_5$ | $OC_2H_5$ | $OC_2H_5$ | 111–119 |
| 4 | S | $C_2H_5$ | $OC_2H_5$ | $OCH_3$ | 172–173* |
| 5 | S | $C_2H_5$ | $OC_2H_5$ | $OC_2H_5$ | 155–159.5 |
| 6 | S | $C_2H_5$ | $C_2H_5$ | $OCH_3$ | 128.5–131* |
| 7 | S | $C_2H_5$ | $C_2H_5$ | $OC_2H_5$ | 151–153.5 |
| 8 | S | $OC_2H_5$ | $OC_2H_5$ | $OCH_3$ | 125–128 |

*decomposed

ANTHELMINTIC TESTS

A 50 percent wettable powder of the test compound was made up with water and dosed orally, by drenching bottle, to sheep, the volume given being approximately 50 ml. per animal.

Dosages of 20 and 40 mg/kg body weight were employed, as shown below. The feces passed by the sheep were collected for a day after treatment and mixed with water so that samples could be taken for estimation of the numbers of small worms expelled, and the whole output sieved for large species.

The sheep were killed three days post-dosing and the worms left in the intestinal tract counted by the usual methods, i.e., dilution counts for the smaller worms and direct sieve counts for the larger ones. The results are given below.

COMPOUND 1

Test 1, 1st sheep: Expelled 0/67 Ostertagia, 0/500 Cooperia, 0/67 Nematodirus, 0/67 Capillaria, 350/350 Trichstrongylus, 0/15 Bunostomum, 11/67 Chabertia, 0/25 Oes. venulosum, 0/38 Trichuris and 0/2 Moniezia.

2nd sheep: Probably expelled some Haemonchus and/or Trichstrongylus. At post-mortem there were 100 Hematodirus, 400 Cooperia, 33 immature Ostertagia and 2 Bunostomum. 3/4 Chabertia were expelled.

Test 2, 1st sheep: Expelled 86/120 Ostertagia, 4700/4733 Trichstrongylus, 86/86 Nematodirus, 0/200 Cooperia, 52/52 Oes. venulosum, 39/39 Chabertia and 0/16 Trichuris.

2nd sheep: Expelled all of the few Haemonchus present, 100/100 Ostertagia, 2500/2500 Trichstrongylus, 50/50 Nematodirus, 83/83 Oes. venulosum, 0/7 Trichuris. Two scolices of Moniezia and an odd liver fluke were found at the post-mortem on day 5.

COMPOUND 2

Tests on two sheep at dosages of 40 mg/kg showed fair-to-good clearance of common nematodes.

COMPOUND 3

Moderate clearance of nematodes in a test on one sheep at 40 mg/kg.

COMPOUND 4

Tests on two sheep at dosages of 40 mg/kg showed fair-to-good clearance of nematodes except for Trichuris, Strongyloides and Moniezia.

COMPOUND 5

Tests on two sheep at dosages of 40 mg/kg showed moderate-to-fair clearance of nematodes.

COMPOUND 6

Tests on two sheep at dosages of 40 mg/kg showed good (>90%) clearance of nematodes except Strongyloides.

COMPOUND 7

A test on one sheep at a dosage of 40 mg/kg expelled 650/700 Trichstrongylus, 0/167 Nematodirus, 0/33 Cooperia, 1/1 Chabertia, 1/36 *Oes. venulosum*, 0/11 Bunostomum, 0/83 Trichuris, and 0/67 Ostertagia. Cooperia larvae and *T. axei* were also found at post-mortem.

COMPOUND 8

Tests on two sheep at a dosage of 40 mg/kg, produced the following results:

1st sheep: expelled 2000/2000 Trichstrongylus, 41/41 Chabertia, 0/33 Cooperia and 0/6 *Oes. venulosum*. 40 Moniezia scolices were found at post-mortem.

2nd sheep: expelled 0/330 Nematodirus but probably most of the other small Trichstrongyles, 4/56 *Oes. venulosum*, 69/71 Chabertia, and 0/30 Trichuris. Some Dictycaulus were found at post-mortem.

Anthelmintic compositions, utilizing as anthelmintic agents compounds according to the present invention, are generally administered directly to animals in the form of solutions, suspensions, powders, tablets, capsules, etc., or the compounds can be admixed to the animal's feed or drinking water.

The compounds of the present invention can be administered to animals already infested with helminths or animals to be protected against helminths in the form of therapeutic preparations either as one single dose or repeatedly, the single dosage depending on the weight of the animal. Preferably, the anthelmintic compound is administered to the animal in an amouunt of between 10 and 100 mg per kg body weight of the animal, most preferably about 40 mg/kg.

To prepare the anthelmintic compound in proper form for administration to the animal there can be used, for example solid carriers, such as kaolin, talcum, calcium phosphate, or feeds or fillers such as fish meal, protein concentrates, soy bean meal, etc. or liquids such as water or oils. The feed mix may also contain other substances beneficial to the animal such as vitamins, minerals, antibiotics, fungicides, hormone preparations or other substances which promote growth, influence the quality of the meat of the animal, or are useful to the animal organism in any other way. One means of incorporating the active substance into the animal's feed is to premix the anthelmintic agent with a small amount of such a carrier and/or other beneficial compounds and then add this premixed formulation to a commercial food such as a mixture of grains, etc.

What is claimed is:

1. A method of controlling helminth infections in animals which comprises orally administering to said animal an anthelmintically effective amount of a compound having the formula

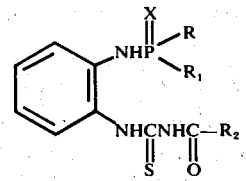

in which X is oxygen or sulfur, R and $R_1$ are independently lower alkyl or lower alkoxy, and $R_2$ is lower alkoxy.

2. A method according to claim 1 in which X is oxygen, R and $R_1$ are ethoxy and $R_2$ is methoxy.

3. A method according to claim 1 in which X is sulfur, R and $R_1$ are ethoxy and $R_2$ is methoxy.

* * * * *